United States Patent
Shick et al.

(10) Patent No.: US 8,343,521 B2
(45) Date of Patent: Jan. 1, 2013

(54) ETHANOL-FREE AQUEOUS PERFUME COMPOSITION

(75) Inventors: Reed A. Shick, Midland, MI (US); Christian Piechocki, Marienthal (FR); Christopher J. Tucker, Midland, MI (US); Letha A. Gatz, Midland, MI (US)

(73) Assignee: Dow Global Technologies, LLC

( * ) Notice: Subject to any disclaimer, the term of this patent is extended or adjusted under 35 U.S.C. 154(b) by 682 days.

(21) Appl. No.: 11/579,301

(22) PCT Filed: Apr. 21, 2005

(86) PCT No.: PCT/US2005/013564
§ 371 (c)(1), (2), (4) Date: Nov. 1, 2006

(87) PCT Pub. No.: WO2005/123028
PCT Pub. Date: Dec. 29, 2005

(65) Prior Publication Data
US 2008/0003247 A1 Jan. 3, 2008

(51) Int. Cl.
*A61K 8/02* (2006.01)
*A61L 9/04* (2006.01)
(52) U.S. Cl. ...................... 424/401; 424/76.4
(58) Field of Classification Search ............ 424/401
See application file for complete search history.

(56) References Cited

U.S. PATENT DOCUMENTS

| | | | |
|---|---|---|---|
| 6,403,109 B1 * | 6/2002 | Stora | 424/401 |
| 6,498,197 B1 | 12/2002 | Blalek et al. | |
| 2001/0053374 A1 | 12/2001 | Dalrymple et al. | |
| 2002/0049149 A1 | 4/2002 | Durbut et al. | |
| 2003/0186836 A1 | 10/2003 | Dumanois et al. | |
| 2004/0077776 A1 | 4/2004 | Feng et al. | |
| 2004/0209795 A1 | 10/2004 | Vlad | |

FOREIGN PATENT DOCUMENTS

| | | |
|---|---|---|
| EP | 0 842 606 | 5/1998 |
| JP | 11-193208 | 7/1999 |
| WO | WO 99/56716 | 11/1999 |
| WO | WO 2004/050045 | 6/2004 |

OTHER PUBLICATIONS

Kahlweit et al., "Preparing Nontoxic Microemulsions", Langmuir 1996, vol. 11, No. 11.
Kahlweit et al., "Preparing Non Toxic Microemulsions with Alkyl Monoglucosides and the Role of Alkandediols as Cosolvents", Langmuir 1996, vol. 12, p. 861-862.
Kahlweit et al., "Preparing Nontoxic Microemulsions. 2", Langmuir 1997, vol. 13, p. 5249-5251.
Kenneth Mason Research Disclosure, "Use of 1,2 Hexanediol as an Evaporative, High Efficicacy, Solvent/Surfactant", XP-000888672,. May 1999.

* cited by examiner

*Primary Examiner* — Sreeni Padmanabhan
*Assistant Examiner* — Layla Soroush

(57) ABSTRACT

The present invention relates to an ethanol-free, non-fatty, non-sticky perfumed aqueous cosmetic microemulsion composition, including one or more fragrance materials, a solvent, an aqueous medium, and optionally, one or more surfactants; wherein the solvent in the microemulsion is a vicinal diol such as 1,2-hexanediol.

6 Claims, No Drawings

ETHANOL-FREE AQUEOUS PERFUME COMPOSITION

BACKGROUND OF THE INVENTION

The present invention relates to a transparent, ethanol-free perfumed aqueous microemulsion composition, such as fragrances, Eaux de Toilettes, body sprays, body deodorants, refreshing and cleaning wet towels, aqueous cosmetic compositions, household cleaners, and air fresheners.

In the perfume industry there has been a long standing need for ethanol-free aqueous perfume compositions. It is well known to produce cosmetic compositions containing ethanol, by the consumers often designated as "alcohol". Such ethanol-containing cosmetics are not acceptable for various reasons such as skin sensitivity, infant safety, and religious prohibition of use of ethanol for some consumers. Also, there is an ongoing trend to reduce the use of volatile organic chemicals (VOC). Aqueous compositions, on the other hand, have the benefits that water is environmentally friendly and the formulations are non-flammable. The perfume industry has attempted to develop ethanol-free compositions to meet the needs of the consumers.

Heretofore, ethanol-free aqueous perfume compositions, the appearance of which can range from that of milk to that of a clear, transparent liquid, generally include the following components: a mixture of natural and/or synthetic fragrance raw materials insoluble in water; an ionic surfactant and/or a non-ionic surfactant; an amphiphilic solubilising agent, such as a polyethylene glycol; an aqueous dispersing agent (generally water); and a preservative. The surfactants in the above compositions are generally present in high doses, and are intended, according to their content, to emulsify or to couple the mixture of fragrance materials.

The above known ethanol-free perfume compositions, generally have the following drawbacks: the compositions are not always transparent; the compositions are sticky owing to the sticky nature of the surfactants and to the relatively large quantity of surfactants implemented; the perfume given off by the fragrance material present in the compositions is liable to be denatured by the solubilising agent; the compositions are somewhat irritant owing to the irritant nature of the solubilising agent and the aggressive nature of the surfactants; and the fragrance material present in the compositions are liable to be deteriorated by air oxidation, which detrimentally affects the stability and the olfactory characteristics of the compositions.

An attempt to eliminate the above drawbacks is disclosed in U.S. Patent Application Publication No. US2003/0186836 A1, published Oct. 2, 2003 wherein an isoprene glycol is used as the microemulsion cosolvent in an ethanol-free perfume composition. The Applicant of the above Patent Application Publication sought to provide a composition with a reduced dose of surfactants that are the origin, in particular, of the sticky and irritant nature of known cosmetic compositions. However, the Applicant was not able to completely eliminate the use of surfactants.

In addition, the composition disclosed in U.S. Patent Application Publication No. US2003/0186836 has other disadvantages: isoprene glycol is not a very amphiphilic solvent, is a poor coupling agent and is not currently listed as a Cosmetic, Toiletry, & Fragrance Association (CTFC) and The International Nomenclature of Cosmetic Ingredients (INCI) acceptable cosmetic ingredient; the composition is limited by the amount of essential oils microemulsified (e.g. 10% by weight maximum); and the composition is limited by a minimum amount of useful surfactant, e.g. 1 wt. % surfactant.

Materials which are previously known and acceptable cosmetic ingredients makes practical the use and acceptance of final formulations containing such materials by cosmetic producers, government agencies and ultimately the consumer. Isoprene glycol has limited acceptance in just a few countries as a cosmetic ingredient.

There is still a need in the cosmetic industry for an ethanol-free aqueous cosmetic composition approved for cosmetic uses that provides efficient, optically clear, non-greasy, non-tacky fragrance microemulsions.

SUMMARY OF THE INVENTION

The present invention is directed to an ethanol-free, transparent, perfumed aqueous microemulsion composition comprising: (A) at least one fragrance material, (B) a solvent, wherein said solvent is a vicinal diol such as 1,2-hexane diol, (C) an aqueous medium, and (D) optionally, one or more surfactants.

The ethanol-free, transparent, perfumed aqueous cosmetic microemulsion composition is generally non-greasy and non-sticky. It is particularly useful as a cosmetic, microemulsion composition. The perfumed aqueous cosmetic microemulsion composition of the present invention, previously long-sought after, is now achieveable by using a specific vicinal diol solvent, such as 1,2-hexanediol, in place of known solubilising agents.

The vicinal diol solvent, for example, 1,2-hexanediol, which is amphiphilic, i.e., both hydrophilic and lipophilic, makes it possible, in fact, thanks to its solvent and solubilising power, to substantially reduce the quantity of surfactants used to arrive at a stable composition. This solvent further has characteristics that are absolutely essential in order to obtain a suitable cosmetic composition. Indeed, the solvent enables translucent compositions to be obtained. In addition, the solvent does not denature the fragrance substance or substances intended for incorporation in said composition in order to obtain a perfumed composition, and the solvent is neither sticky, nor irritant, nor sensitive to air oxidation.

DETAILED DESCRIPTION OF THE PREFERRED EMBODIMENTS

"Ethanol-free" when used herein in reference to a substance means substantially free of ethyl alcohol. "Substantially free" in this context means less than 3 wt %, preferably less than 1 wt %, and more preferably zero weight percent present in a substance.

A "microemulsion" as the term is used herein denotes a pseudo one-phase transparent mixture of (i) two immiscible fluids, and (ii) at least one amphiphile (exemplified by surfactants). Microemulsions are transparent or translucent, and do not display the opalescence of standard emulsions. The particle size of the resulting droplets is small enough so the resulting mixture is optically clear or translucent. Microemulsion droplet sizes are variously defined in the art with a droplet size typically below 0.14 micron. The clarity of these compositions is advantageous in cosmetic applications. Also, microemulsions are thermodynamically stable and form spontaneously.

For the purposes of the present invention, the term "optically clear" is used to define a composition that is "transparent" (i.e. transmitting light without distortion) which means that the size of the particles in the composition are reduced to a size where the particles are not observable with optical (visual) means. Transmitting light without distortion as used herein means being able to read 12-point text through a 1-centimeter thick sample of the microemulsion.

The ethanol-free, perfumed aqueous microemulsion composition of the present invention includes the following components: (A) one or more fragrance raw materials, (B) a solvent, wherein said solvent is a vicinal diol, (C) an aqueous medium, and (D) optionally, one or more surfactants. The present invention may also optionally contain one or more additional ingredients, such as antioxidants, chelating agents, UV filters, preservatives, thickening agents, cosmetic active ingredients, moisturizers, humectants, emollients, opacifiers, pearly gloss impacting substances, pigments, colorants, dyes and antifoams.

The perfumed aqueous microemulsion composition of the present invention includes one or more fragrance materials, Component (A), such as natural and/or synthetic fragrance raw materials. Of particular interest are oil soluble perfume oils, which may or may not be in a mixture with water soluble perfume oils. The oil soluble perfume oils are natural, or nature-identical essential oils, such as orange oil, pine oil, peppermint oil, eucalyptus oil, lemon oil, clove leaf oil, cedarwood oil, bergamot oil, rosemary oil, patchouli oil, lavandin oil, camomile, jasmine oil, spike oil, rose oil, vetiver oil, fennel oil, anise oil, thyme oil, germanium oil, lavender oil, marjoram or menthol. An animal fragrant, is for example musk, castoreum, aber or zibet. Spagyric essences are also known in the art. They are made by fermenting certain herbs, which were collected while they were flowering, in the presence of water and yeast, steam distilling off the active ingredients, and concentrating the distilate to the spagyric basic essence. The remaining mash is calcinated, and the basic essence and the calcinated mash are combined to give the final spagyric essence. Synthetic fragrant ingredients are for example synthetic essential oils, such as composed of single compounds, such as linalol, terpineol, nerol, cit-ronelal, benzaldehyde, cinnamon aldehyde, vanillin or methylacetophenone. The fragrance materials may also be synthetic oil-soluble perfume oils, selected from the usual group consisting of fragrant hydrocarbons, alcohols, ketones, aldehydes, ethers, esters, aldehydes, acetals and polyene compounds. Naturally, this term also encompasses any mixture of perfume oils described above, or perfume concentrates or bases with preferably non-ethanolic diluents. Illustrative examples of Component (A) may include commercially available fragrance compositions such as MUSTANG M 0054401, THOMAS M 0054402, BLISS M 0054403, CRACK M 0054404, and CITRUS FUSION M 0054405 (all trade names of V. MANE Fils S. A.).

The perfumed aqueous microemulsion composition will advantageously include from about 1% by weight (wt. %) to about 50 wt. %, preferably from about 1% by weight (wt. %) to about 30 wt. %, and most preferably about 2 wt. % to about 30 wt. % of such fragrance materials.

The solvent, Component (B), useful in the present invention includes vicinal diols, for example linear alkane vicinal diols, most preferably linear alkane vicinal diols having from 5 to 8 carbon atoms. For example the solvent may include 1,2-pentanediol; 1,2-hexanediol; 1,2-heptanediol; 1,2-octanediol; and mixtures thereof. Preferably, the solvent used in the present invention is 1,2-hexanediol.

The amount of solvent present in the composition is generally from about 1% by weight to about 50 wt. %, preferably from about 1 wt. % to about 25 wt. %, more preferably from about 3 wt. % to about 20 wt. %, and most preferably from about 5 wt. % to about 15 wt. %.

The aqueous medium, Component (C), useful in the present invention, includes for example at least water and more preferably water stabilized with one or more optional ingredients such as antioxidants, chelating agents, UV filters, and preservatives. Additional ingredients such as thickening agents, cosmetic active ingredients, moisturizers, humectants, emollients, opacifiers, pearly gloss impacting substances, pigments, colorants, dyes and antifoams may also be included in the aqueous medium of composition of the present invention.

The amount of aqueous medium present in the composition is generally from about 50 wt. % to about 95 wt. %, preferably from about 55 wt. % to about 90 wt. % and more preferably from about 60 wt. % to about 85 wt. %.

The use of surfactants, Component (D), in the composition of the present invention is optional. Surprisingly, the vicinal diol can be used in combination with a large variety of surfactants for achieving a clear, transparent microemulsion. Surfactants useful in the present invention, Component (D), include for example cationic, anionic, non-ionic, zwitterionic, amphophilic, or polymeric surfactants, and mixtures thereof. Preferred surfactants include mixtures of non-ionic surfactants and anionic surfactants, mixtures of non-ionic surfactants and cationic surfactants, and mixtures of non-ionic surfactants and zwitterionic surfactants.

Anionic surfactants useful herein are disclosed in U.S. Pat. No. 4,285,841, Barrat et al, issued Aug. 25, 1981, and in U.S. Pat. No. 3,919,678, Laughlin et al, issued Dec. 30, 1975. Preferred anionic surfactants include $C_{11}$-$C_{18}$ alkyl benzene sulfonates and primary or branched-chain $C_{10}$-$C_{20}$ alkyl sulfates, unsaturated sulfates such as oleyl sulfate, the $C_{10}$-$C_{18}$ alkyl alkoxy sulfates, particularly those comprising 1-7 ethoxy groups, $C_{10}$-$C_{18}$ alkyl alkoxy carboxylates, particularly those comprising 1-5 ethoxy groups, the $C_{10}$-$C_{18}$ glycerol ethers, the $C_{10}$-$C_{18}$ alkyl polyglycosides and their corresponding sulfated polyglycosides, and $C_{12}$-$C_{18}$ alpha-sulfonated fatty acid esters. Other useful anionic surfactants include water-soluble salts, particularly the alkali metal, ammonium and alkylolammonium salts, such as monoethanolammonium or triethanolammonium salts, of organic sulfuric reaction products having in their molecular structure an alkyl group containing from about 10 to about 20 carbon atoms and a sulfonic acid or sulfuric acid ester group. Other anionic surfactants useful herein are the water-soluble salts of alkyl phenol ethylene oxide ether sulfates and water-soluble salts of esters of alpha-sulfonated fatty acids. The anionic surfactants based on fatty acids include saturated and/or unsaturated fatty acids obtained from natural sources or synthetically prepared. Examples of suitable fatty acids include, but are not limited to, capric, lauric, myristic, palmitic, stearic, arachidic, and behenic acid. Other fatty acids include palmitoleic, oleic, linoleic, linolenic, and ricinoleic acid.

Suitable nonionic surfactants are disclosed in U.S. Pat. No. 3,929,678, Laughlin et al., issued Dec. 30, 1975, and U.S. Pat. No. 4,285,841, Barrat et al, issued Aug. 25, 1981. Exemplary, non-limiting classes of useful nonionic surfactants include $C_8$-$C_{18}$ alkyl ethoxylates, with about 1-22 ethylene oxide units, including the so-called narrow peaked alkyl ethoxylates and $C_6$-$C_{12}$ alkyl phenol alkoxylates, particularly ethoxylates and mixed ethoxylates/propoxylates, alkyl dialkyl amine oxides, alkanoyl glucose amides, and mixtures thereof. Other useful nonionic surfactants are polyethylene, polypropylene, and polybutylene oxide condensates of alkyl phenols. Commercially available nonionic surfactants of this type include Igepal® CO-630, marketed by the GAF Corporation; and Triton® X45, X-114, X-100, and X-102, all marketed by the Rohm & Haas Company. These compounds are commonly referred to as alkyl phenol alkoxylates, preferably alkyl phenol ethoxylates. Further useful nonionic surfactants are the condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Examples of commercially available nonionic surfactants of this type include Tergitol® 15-S-9 (the condensation product of $C_{11}$-$C_{15}$ linear secondary alcohol with 9 moles ethylene oxide), Tergitol® 24-L-6 NMW (the condensation product of $C_{12}$-$C_{14}$ primary alcohol with 6 moles ethylene oxide with a narrow molecular weight distribution), both marketed by The Dow Chemical Corporation; Neodol® 45-9 (the condensation product of $C_{14}$-$C_{15}$ linear alcohol with 9 moles of ethylene oxide), Neodol® 23-6.5 (the condensation product of $C_{12}$-$C_{13}$ linear alcohol with 6.5 moles of ethylene oxide), Neodol® 45-7 (the condensation product of $C_{14}$-$C_{15}$ linear alcohol with 7 moles of ethylene oxide), Neodol® 45-4 (the condensation product of $C_{14}$-$C_{15}$ linear alcohol with 4 moles of ethylene oxide), marketed by Shell Chemical Company, and Kyro® EOB (the condensation product of $C_{13}$-$C_{15}$ alcohol with 9 moles ethylene oxide), marketed by The Procter & Gamble Company. Other commercially available nonionic surfactants include Dobanol 91-8® marketed by Shell Chemical Co. and Genapol UD-080® marketed by Hoechst. This category of nonionic surfactant is referred to generally as "alkyl ethoxylates." Other useful nonionic surfactants are the condensation products of ethylene oxide with a hydrophobic base formed by the condensation of propylene oxide with propylene glycol. Examples of compounds of this type include certain of the commercially-available Pluronic® surfactants, marketed by BASF. Further useful surfactants are the condensation products of ethylene oxide with the product resulting from the reaction of propylene oxide and ethylenediamine. Examples of this type of nonionic surfactants include certain of the commercially available Tetronic® compounds, marketed by BASF. Semi-polar nonionic surfactants are a special category of nonionic surfactants which include water-soluble amine oxides. These amine oxide surfactants in particular include $C_{10}$-$C_{18}$ alkyl dimethyl amine oxides and $C_{8}$-$C_{12}$ alkoxy ethyl dihydroxy ethyl amine oxides. Other nonionic surfactants are alkylpolysaccharides. Any reducing saccharide containing 5 or 6 carbon atoms can be used, e.g., glucose, galactose and galactosyl moieties can be substituted for the glucosyl moieties. Fatty acid amide surfactants, $C_{12}$-$C_{18}$ betaines and sulfobetaines (sultaines) are also knows surfactants.

Suitable cationic surfactants include the ammonium surfactants such as alkyltrimethyl ammonium halogenides. Examples of suitable quaternary ammonium compounds include, but are not limited to, coconut trimethyl ammonium chloride or bromide; coconut methyl dihydroxyethyl ammonium chloride or bromide; decyl triethyl ammonium chloride; decyl dimethyl hydroxyethyl ammonium chloride or bromide; $C_{12\text{-}15}$ dimethyl hydroxyethyl ammonium chloride or bromide; coconut dimethyl hydroxyethyl ammonium chloride or bromide; myristyl trimethyl ammonium methyl sulphate; lauryl dimethyl benzyl ammonium chloride or bromide; lauryl dimethyl (ethenoxy) 4 ammonium chloride or bromide; and choline esters.

Further useful surfactants are amine oxide surfactants. Commercially available amine oxides are the solid, dihydrate ADMOX 16 and ADMOX 18, ADMOX 12 and especially ADMOX 14 from Ethyl Corp. Other surfactants include dodecyidimethylamine oxide dihydrate, hexadecyidimethylamine oxide dihydrate, octadecyidimethylamine oxide dihydrate, hexadecyltris(ethyleneoxy)dimethyl-amine oxide, tetradecyidimethylamine oxide dihydrate, and mixtures thereof Other useful surfactants are biodegradably branched surfactants are more fully disclosed in WO98/23712 A published Jun. 4, 1998; WO97/38957 A published Oct. 23, 1997; WO97/38956 A published Oct. 23, 1997; WO97/39091 A published Oct. 23, 1997; WO97/39089 A published Oct. 23, 1997; WO97/39088 A published Oct. 23, 1997; WO97/39087 A1 published Oct. 23, 1997; WO97/38972 A published Oct. 23, 1997; WO 98/23566 A Shell, published Jun. 4, 1998.

Useful amphophilic surfactants can be broadly described as aliphatic derivatives of secondary or tertiary amines, or aliphatic derivatives of heterocyclic secondary and tertiary amines in which the aliphatic radical can be straight chain or branched.

Furthermore, the cosmetic microemulsion compositions described herein may contain a polyhydroxy fatty acid amide surfactant. Useful zwitterionic surfactants are described in U.S. Pat. No. 3,929,678. Diamine surfactants may also be used.

Examples of particularly preferred surfactants are ethyloxalated alkanes, fatty acids, fatty acid salts, sulfonates or quaternary ammonium salts, and especially polyoxyethylene fatty ether surfactants, stearic acid and stearic acid salts, most preferably the sodium salt of stearic acid, sodium lauryl sulfate (SLS), sodium laureth sulfate (SLES), lauryl trimethyl ammonium chloride, Brij 30 (trademark of Uniqema, Chemical Abstracts name Poly(oxy-1,2-ethanediyl), alpha-dodecyl-omega-hydroxy-(9CI), Registry Number 9002-92-0), cetyl trimethyl ammonium chloride, or combinations thereof.

The amount of surfactant which may be used in the composition of the present invention is generally from 0 wt. % to about 50 wt. %, preferably from 0 wt. % to about 20 wt. %, more preferably from 0 to about 15 wt. % and most preferably from 0 to about 10 wt. %; and when the surfactant is present in the composition, the amount of surfactant is preferably from about 0.1 wt. % to about 15 wt. %, and more preferably from about 0.5 wt. % to about 10 wt. %.

The weight ratio between the fragrance material and the surfactant, if present in the composition of the present invention, generally is from 0.2:1 to 10:1, preferably from 0.5:1 to 6:1, more preferably from 1:1 to 5:1, and most preferably from 2:1 to 4:1.

Other ingredients that may optionally be present in the composition of the present invention may include for example antioxidants, chelating agents, UV filters, and preservatives. Additional ingredients such as thickening agents, cosmetic active ingredients, moisturizers, humectants, emollients, opacifiers, pearly gloss impacting substances, pigments, colorants, dyes and antifoams may also be optionally used in the composition of the present invention.

The optional additional ingredients are generally present in the composition of the present invention from about 0 wt % to about 5 wt %, preferably from about 0.5 wt % to about 3 wt %, and more preferably from about 0.1 wt % to about 1 wt %.

In one illustration of the composition of the present invention, the composition advantageously includes 1,2-hexanediol in a proportion of from about 5 wt % to 30 wt %; a surfactant, wherein the surfactant is preferably a combination of (i) Brij 30 in a proportion of approximately 0.5 wt % to 5.0 wt % and (ii) stearic acid, sodium lauryl sulfate, sodium laureth sulfate, cetyl trimethyl ammonium chloride or a stearic acid salt in a proportion of approximately 0.5 wt % to 5.0 wt %; and an essential oil in a proportion of approximately 0.5 wt % to 20 wt %; with the remainder being essentially purified water.

All percentages given herein are by the total weight of the perfumed aqueous microemulsion composition.

The microemulsion perfumed aqueous cosmetic composition according to the present invention may be prepared, for example, by simple mixing of all the ingredients; for example by hand stirring or if need be by using a mechanical mixer (i.e. by some mechanically agitating means), the components of the present invention, and any optional components, to form a homogeneous mixture. The components of the present invention may be added together into a suitable reaction vessel and mixed in any order, using conventional processes well known to those skilled in the art. The microemulsion may be produced at room temperature or at an elevated temperature, for example up to 90° C., preferably up to 55° C. can be employed.

The perfume microemulsion compositions of the present invention containing 1,2-hexanediol are uniquely useful. The 1,2-hexanediol as a cosolvent has low odor, pleasant skin feel, and can be formulated as clear stable perfumes with high fragrance loading, in several different product forms.

Because 1,2-hexanediol has very low odor it does not change the olfactory profile of the perfume. This allows perfumers to retain the desired odor profile of fully formulated perfumes.

The 1,2-hexanediol containing perfume microemulsions contain low or no surfactant and as such are pleasant to use with a smooth emollient-like feel without the greasy or tackiness of most presently known perfume microemulsions.

1,2-Hexanediol is known to be an acceptable cosmetic ingredient by CTFC and INCI. The use of 1,2-hexanediol as a microemulsion cosolvent is described in U.S. Pat. No. 6,498,197 and U.S. Patent Application Publication No. US2004/0077776 A1 for silicone microemulsions suitable for cosmetics. Clear hair conditioning microemulsions including 1,2-hexanediol cosolvent are described in U.S. Patent Application Publication No. US2001/0053374 A1. However, 1,2-hexanediol has never been developed as a cosolvent for a perfume microemulsion, 1,2-hexanediol's unexpected sensory benefits were unknown, and the use of 1,2-hexanediol in surfactant-free compositions were unknown prior to the present invention.

The 1,2-hexanediol containing perfume microemulsions can be formulated to be optically clear, and stable from about 5° C. to about 55° C.; and to contain a wide variety of fragrance loadings, for example, from about 1 percent by weight to about 30 percent by weight essential oils.

Fragrances, Eaux de Toilettes, aqueous perfumes, body sprays, body deodorants as well as products such as refreshing and cleaning wet towels, aqueous cosmetic compositions, household cleaners, air fresheners and sprayable formulations all require different fragrance loading, and are all easily made using the present invention. A single properly formulated perfume microemulsion containing 1,2-hexanediol may be diluted for example from about 50 wt. %, preferably from about 30 wt. % to about 1 wt. % with no loss of stability, i.e. the resulting product is maintained as a microemulsion. Furthermore, perfume microemulsions containing 1,2-hexanediol can be made stable in spite of the addition of other ingredients such as dyes, gelling agents, iridescent material or sparkling materials.

The following examples are given to illustrate the present invention. Because these examples are given for illustrative purposes only, the present invention embodied herein should not be limited thereto.

Examples of perfumed aqueous cosmetic compositions according to the present invention are given below by way of non-limitative illustration. Onless otherwise indicated all parts and percentages are by weight.

EXAMPLE 1

The ingredients used in this Example 1 were as follows:
Surfactants: Brij 30 (trademark of Uniqema)
Sodium Stearate
Cosolvent: 1,2-hexanediol
Aqueous Medium: Water
Fragrance: MUSTANG M 0054401
General Procedure Into a 15 mL glass container, 0.1 g of stearic acid, 0.1 g of Brij 30, 1 g of 1,2-hexanediol, and 0.35 g of a 1 N NaOH solution are introduced at room temperature (about 20° C.).

The resulting blend in the container is gently shaken while heated up to 40-50° C. until a clear homogeneous solution is obtained. This takes only a few minutes (about less than 5 minutes). The container is cooled back to room temperature in a water bath. Once at room temperature, 0.6 g of MUSTANG M 0054401 is added to the container. Again, a clear homogeneous solution is obtained.

Then 7.6 g of pure water is added to the container. Towards the end of addition of water, the solution becomes turbid (milky white). Dropwise addition of 1,2-hexanediol is carried out until the solution becomes optically clear and homogeneous. It takes 0.238 g of 1,2-hexanediol to achieve the optically clear and homogeneous solution.

The weight composition of the resulting aqueous perfume produced according to the above general procedure is as follows:
12.36% 1,2-hexanediol
1% Brij 30
1% stearic acid
6% MUSTANG M 0054401
79.51% water
0.14% NaOH

EXAMPLE 2

Using the same general procedure as described in Example 1 above, 220 g of a 6% stabilized MUSTANG M 0054401 aqueous perfume were produced in this Example 2 with the following quantities of raw materials:
28.48 g 1,2-hexanediol (12.98%)
2.32 g Brij 30 (1.06%)
2.32 g stearic acid (1.06%)
13.95 g MUSTANG M 0054401* (6.36%)
172.02 g water** (78.40%)
0.33 gNaOH pure (0.15%)
*containing 0.3% UV filter and 0.1% antioxidant
**water contained 0.2% Biocide and 0.1% EDTA

EXAMPLE 3

The same ingredients and general procedure as described in Example 1 were used in this Example 3, except that the fragrance was BLISS M 0054403, to produce an aqueous perfume having the following composition:
10.27% 1,2-hexanediol (22.59 g)
0.57% Brij 30 (1.247 g)
0.57% stearic acid (1.247 g)
3.40% BLISS M 0054403* (7.48 g)
85.11% stabilized water**(187.18 g)
0.08% pure NaOH (0.175 g)
*containing 0.3% UV filter and 0.1% antioxidant
**water contained 0.2% Biocide and 0.1% EDTA

EXAMPLE 4

The same ingredients and general procedure as described in Example 1 were used in this Example 4, except that THOMAS M0054402 fragrance was used, to produce an aqueous perfume having the following composition:
- 11.45% 1,2-hexanediol (25.08 g)
- 0.42% Brij 30 (0.918 g)
- 1.68% stearic acid (3.673 g)
- 6.29% THOMAS M0054402* (13.77 g)
- 79.94% water** (175.13 g)
- 0.24% pure NaOH (0.516 g)

*containing 0.3% UV filter and 0.1% antioxidant
**water contained 0.2% Biocide and 0.1% EDTA

EXAMPLE 5

Similar ingredients and the same general procedure as described in Example 1 were used in this Example 5, except that CITRUS FUSION M 0054405 fragrance was used, to produce an aqueous perfume having following composition:
- 7.71% 1,2-hexanediol (0.5 g)
- 3.86% Brij 30 (0.25 g)
- 3.86% stearic acid (0.25 g)
- 23.14% CITRUS FUSION M 0054405 (1.5 g)
- 59.40% water (175.13 g)
- 2.02% triethanolamine (0.131 g)

EXAMPLE 6

The same general procedure as described in Example 1 was used in this Example 6, except that 1,2-hexanediol, CRACK M 0054404 fragrance and water were used to produce an aqueous perfume having the following surfactant-free composition:
- 19.08% 1,2-hexanediol (0.95 g)
- 16.07% CRACK M 0054404 (0.80 g)
- 64.85% water (3.23 g)

EXAMPLE 7

Using the same general procedure as described in Example 1, 5 g of a 5% stabilized LEA* M 0045414 aqueous perfume were produced with the following quantities of raw materials:
- 0.73 g 1,2-hexanediol (14.6%)
- 0.042 g Brij 30 (0.83%)
- 0.042 g stearic acid (0.83%)
- 0.25 g LEA* M 0045414 (5.00%)
- 3.93 g water** (78.62%)
- 0.006 gNaOH pure (0.12%)

*containing 0.3% UV filter and 0.1% antioxidant
**water contained 0.2% Biocide and 0.1% EDTA
Stearic acid can be replaced by SLS (sodium lauryl sulfate) or cetyl trimethyl ammonium chloride as shown in Examples 8 and 9.

EXAMPLE 8

Into a 15 mL glass container, 0.139 g of SLS (sodium lauryl sulfate, 30% active in water), 0.042 g of Brij 30, 0.2 g of 1,2-hexanediol, and 0.5 g of water were introduced at room temperature (about 20° C.).

The resulting blend in the container was gently shaken to afford a clear homogeneous solution. This took less than 5 minutes. 0.25 g of LEA* M 0045414 fragrance was added to the container which was gently shaken to homogenize. A clear homogeneous solution was obtained. Then 3.34 g of pure water was added to the container. Towards the end of addition of water, the solution became turbid (milky white). Dropwise addition of 1,2-hexanediol was carried out until the solution became optically clear and homogeneous. It took 0.54 g of 1,2-hexanediol to achieve an optically clear, transparent microemulsion.

The weight composition of the resulting aqueous perfume produced according to the above procedure was as follows:
- 14.80% 1,2-hexanediol
- 0.84% Brij 30
- 0.84% SLS
- 4.99% LEA* M 0045414
- 78.54% water.

The composition of the aqueous microemulsion was very similar to the composition of Example 7, except that no sodium hydroxide was used and no heat was applied to prepare the sample.

EXAMPLE 9

Into a 15 mL glass container, 0.167 g of cetyl trimethyl ammonium chloride (25% active in water), 0.042 g of Brij 30, 0.2 g of 1,2-hexanediol, and 0.5 g of water were introduced at room temperature (about 20° C.).

The resulting blend in the container was gently shaken to afford a clear homogeneous solution. This took less than 5 minutes. 0.25 g of LEA* M 0045414 was added to the container which was gently shaken to homogeneise. A clear homogeneous solution was obtained. Then 3.34 g of pure water was added to the container. Towards the end of addition of water, the solution became turbid (milky white). Dropwise addition of 1,2-hexanediol was carried out until the composition became optically clear. It took 0.537 g of 1,2-hexanediol to achieve an optically clear and transparent microemulsion.

The weight composition of the resulting aqueous perfume produced according to the above procedure was as follows:
- 14.72% 1,2-hexanediol
- 0.84% Brij 30
- 0.84% cetyl trimethyl ammonium chloride
- 4.99% LEA* M 0045414
- 78.61% water The composition of the aqueous microemulsion of Example 9 was very similar to the composition of Example 7, except that no sodium hydroxide was used and no heat applied to prepare the sample.

EXAMPLE 10

Similar ingredients and the same general procedure as described in Example 7 were used in this Example 10, except that CITRUS FUSION M 0054405 fragrance was used, to produce an aqueous perfume having following composition:
- 7.96% 1,2-hexanediol (0.400 g)
- 0.83% Brij 30 (0.042 g)
- 0.83% stearic acid (0.042 g)
- 4.98% CITRUS FUSION M 0054405 (0.250 g)
- 85.29% water (4.286 g)
- 0.12% NaOH pure (0.006 g)

Stearic acid can be replaced by SLS (sodium lauryl sulfate) or cetyl trimetyl ammonium chloride as shown in Examples 11 and 12.

EXAMPLE 11

Similar ingredients and the same general procedure as described in Example 8 were used in this Example 11, except that CITRUS FUSION M 0054405 fragrance was used, to produce an aqueous perfume having following composition:
- 9.53% 1,2-hexanediol (0.45 g)
- 0.89% Brij 30 (0.042 g)
- 0.89% SLS (0.042 g)
- 5.30% CITRUS FUSION M 0054405 (0.25 g)
- 83.39% water (3.937 g)

The composition of the aqueous microemulsion of Example 11 was very similar to the composition of Example 10, except that no sodium hydroxide was used and no heat applied to prepare the sample.

EXAMPLE 12

Similar ingredients and the same general procedure as described in Example 9 were used in this Example 12, except that CITRUS FUSION M 0054405 fragrance was used, to produce an aqueous perfume having the following composition:
- 10.05% 1,2-hexanediol (0.477 g)
- 0.88% Brij 30 (0.042 g)
- 0.88% cetyl trimethyl ammonium chloride (0.042 g)
- 5.27% CITRUS FUSION M 0054405 (0.25 g)
- 82.92% water (3.937 g)

The composition of the aqueous microemulsion of Example 12 was very similar to composition of Example 10, except that no sodium hydroxide was used and no heat was applied to prepare the sample.

EXAMPLE 13

Similar ingredients and the same general procedure as described in Example 8 were used in this Example 13, except that 1,2-heptane diol instead of 1,2-hexane diol was used to produce an aqueous perfume the having following composition:
- 11.78% 1,2-heptane diol
- 0.91% Brij 30
- 0.81% SLS (sodium lauryl sulfate)
- 5.14% fragrance LEA I 871382 DPG free
- 81.37% water.

An optically clear and transparent microemulsion was obtained.

EXAMPLE 14

Similar ingredients and the same general procedure as described in Example 8 were used in this Example 14, except that 1,2-heptane diol instead of 1,2-hexane diol was used to produce an aqueous perfume having following composition:
- 17.12% 1,2-hexane diol
- 0.88% Brij 30
- 0.78% SLS (sodium lauryl sulfate)
- 4.86% fragrance LEA I 871382 DPG free
- 76.36% water.

An optically clear and transparent microemulsion was obtained.

While the present invention has been particularly shown and described with respect to preferred embodiments thereof, it will be understood by those skilled in the art that the foregoing and other changes in the form and detail may be made without departing from the spirit and scope of the present invention. It is therefore intended that the present invention not be limited to the exact forms and details described and illustrated, but fall within the appended claims.

What is claimed is:

1. An ethanol-free, transparent, perfumed aqueous microemulsion composition comprising:
   (A) a fragrance material, wherein the fragrance material is present in an amount greater than 5% and less than 50% by weight;
   (B) a solvent, wherein said solvent is 1,2-hexanediol or 1,2-heptanediol; and
   (C) an aqueous medium;
   wherein the composition does not contain surfactants.

2. The composition of claim 1 wherein the solvent is 1,2-hexanediol.

3. The composition of claim 1, wherein the solvent is present in an amount of from 1% to 50% by weight.

4. The composition of claim 3, wherein the solvent is present in an amount of from 1% to 25% by weight.

5. The composition of claim 1, wherein the aqueous medium is present in an amount of from 50% to 95% by weight.

6. The composition of claim 1, wherein the fragrance material is a natural essential oil, synthetic essential oil or a mixture thereof.

* * * * *